United States Patent [19]
Ouchi

[11] Patent Number: 6,093,155
[45] Date of Patent: Jul. 25, 2000

[54] CYTOLOGIC BRUSH FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/241,064

[22] Filed: Feb. 1, 1999

[30] Foreign Application Priority Data

Feb. 13, 1998 [JP] Japan ................................ P10-031043

[51] Int. Cl.⁷ .................................................. A61B 10/00
[52] U.S. Cl. ........................................... 600/569; 606/205
[58] Field of Search ................................... 600/569, 510; 606/205, 207

[56] References Cited

U.S. PATENT DOCUMENTS

| | | | |
|---|---|---|---|
| 2,739,585 | 3/1956 | Ayre | ......................................... 600/569 |
| 4,271,845 | 6/1981 | Chikashige et al. . | |
| 4,982,727 | 1/1991 | Sato | ....................................... 606/205 |

FOREIGN PATENT DOCUMENTS

| | | |
|---|---|---|
| 56-10329 | 3/1981 | Japan . |
| 59-17286 | 5/1984 | Japan . |
| 3-56414 | 5/1991 | Japan . |
| 5-142 | 1/1993 | Japan . |

Primary Examiner—Cary O'Connor
Assistant Examiner—Pamela Wingood
Attorney, Agent, or Firm—Greenblum & Bernstein, P.L.C.

[57] ABSTRACT

A cytologic brush for an endoscope has a flexible sheath removably inserted into an instrument-inserting channel. A brush member is provided at the distal end of the sheath. A single control wire is inserted in the sheath to change the direction of the brush member from the proximal end of the sheath. The proximal end of the brush member is connected to a forward link member of a link mechanism provided at the distal end of the sheath. The distal end of the control wire is connected to the rear end of the link mechanism. By moving the control wire back and forth at an operating part connected to the proximal end of the sheath, the link mechanism is operated to change the direction of the brush member with respect to the distal end of the sheath.

7 Claims, 8 Drawing Sheets

CYTOLOGIC BRUSH FOR ENDOSCOPE

BACKGROUND OF THE INVENTION

The present disclosure relates to subject matter contained in Japanese Patent Application No. 10-31043 (filed on Feb. 13, 1998), which is expressly incorporated herein by reference in its entirety.

1. Field of the Invention

The present invention relates to a cytologic brush for an endoscope which has a brush member attached to the distal end of a sheath that is removably inserted into an instrument-inserting channel of the endoscope. More particularly, the present invention relates to a cytologic brush for an endoscope that is designed so that the direction of the brush member can be changed by remote control from the proximal end of the sheath.

2. Description of the Prior Art

Cytologic brushes for endoscopes are widely used to perform a scraping cytodiagnosis, in which cells are collected from the mucous membrane surface of a bronchial tube or the like. A typical cytologic brush has a brush member attached to the distal end of a sheath that is removably inserted into an instrument-inserting channel of an endoscope.

There are conventional cytologic brushes arranged so that the direction of the brush member can be changed by pulling a control wire, which is connected to the brush member and inserted in the sheath, from the proximal end of the sheath, thereby enabling a cell collecting location to be selected as desired.

In all the conventional cytologic brushes that can be reoriented, the direction of the brush member is changed by bending the distal end portion of the sheath. During the reorientation of the brush member, the control wire, which is inserted in the sheath, is also bent together with the sheath. Therefore, in the course of using the brush repeatedly, the control wire develops an undesired bending habit. Consequently, the brush member becomes incapable of extending straight ahead and hence difficult to use.

Figure 8:
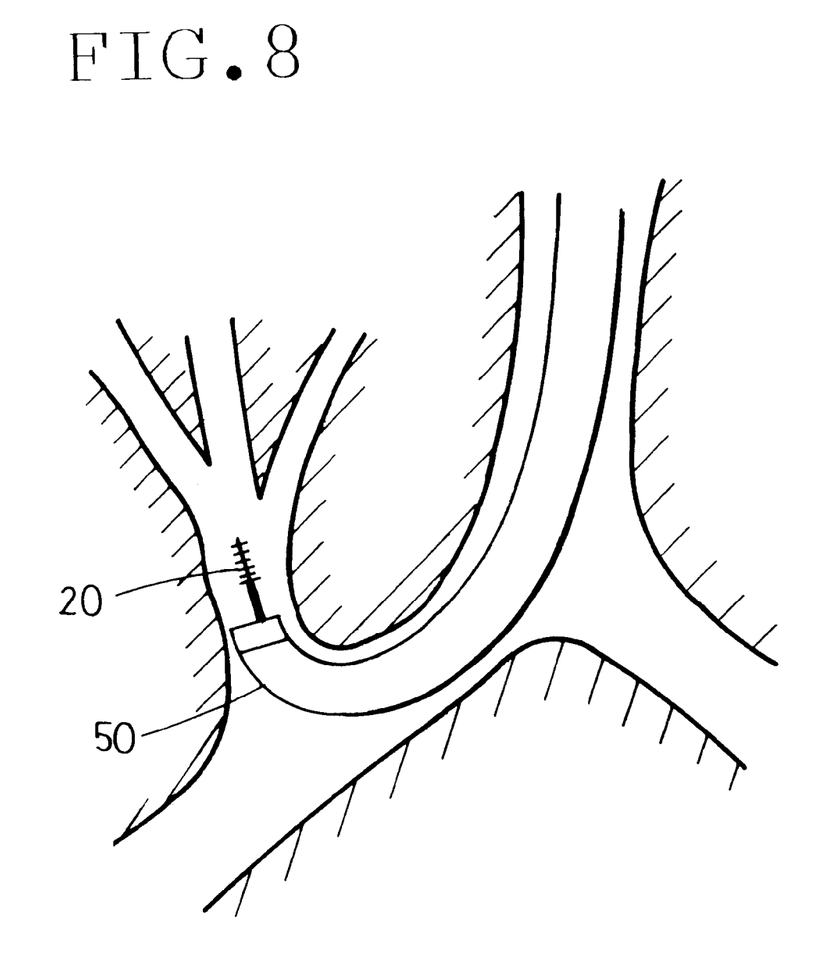
FIG. 8 is a schematic view showing a cytologic brush for an endoscope as used in a bronchial tube.

The conventional cytologic brushes further have the disadvantage that the direction of the brush member can be changed in only one direction from the extension direction of the axis of the distal end portion of the sheath (i.e. from a position where the brush member extends straight ahead). Therefore, in a trifurcated deep bronchial tube as shown in FIG. 8 by way of example, a brush member 20 projecting from the distal end of an endoscope 50 can be inserted into either of two tubes, i.e. one that lies in front of the brush member 20, and another that lies in a direction to which the brush member 20 can be deflected. Thus, the inspection range is unfavorably limited.

SUMMARY OF THE INVENTION

An object of the present invention is to provide a cytologic brush for an endoscope that is designed so that even when the operation of changing the direction of the brush member is repeated, the control wire will not develop an undesired bending habit, and the brush member can be reoriented so as to be inserted into a narrow tubular cavity in a desired direction.

Other objects and advantages of the present invention will become apparent from the following detailed description of illustrated embodiments of the invention.

According to the present invention, there is provided a cytologic brush for an endoscope which has a flexible sheath removably inserted into an instrument-inserting channel of the endoscope. A brush member is provided at the distal end of the sheath. A single control wire is inserted in the sheath to change the direction of the brush member from the proximal end of the sheath. The cytologic brush includes a link mechanism provided at the distal end of the sheath. The proximal end of the brush member is connected to a forward link member of the link mechanism. The distal end of the control wire is connected to the rear end of the link mechanism. An operating part is connected to the proximal end of the sheath to move the control wire back and forth. Thus, by moving the control wire back and forth at the operating part, the link mechanism is operated to change the direction of the brush member with respect to the distal end of the sheath.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

An embodiment of the present invention will be described below with reference to the accompanying drawings.

Figure 1:
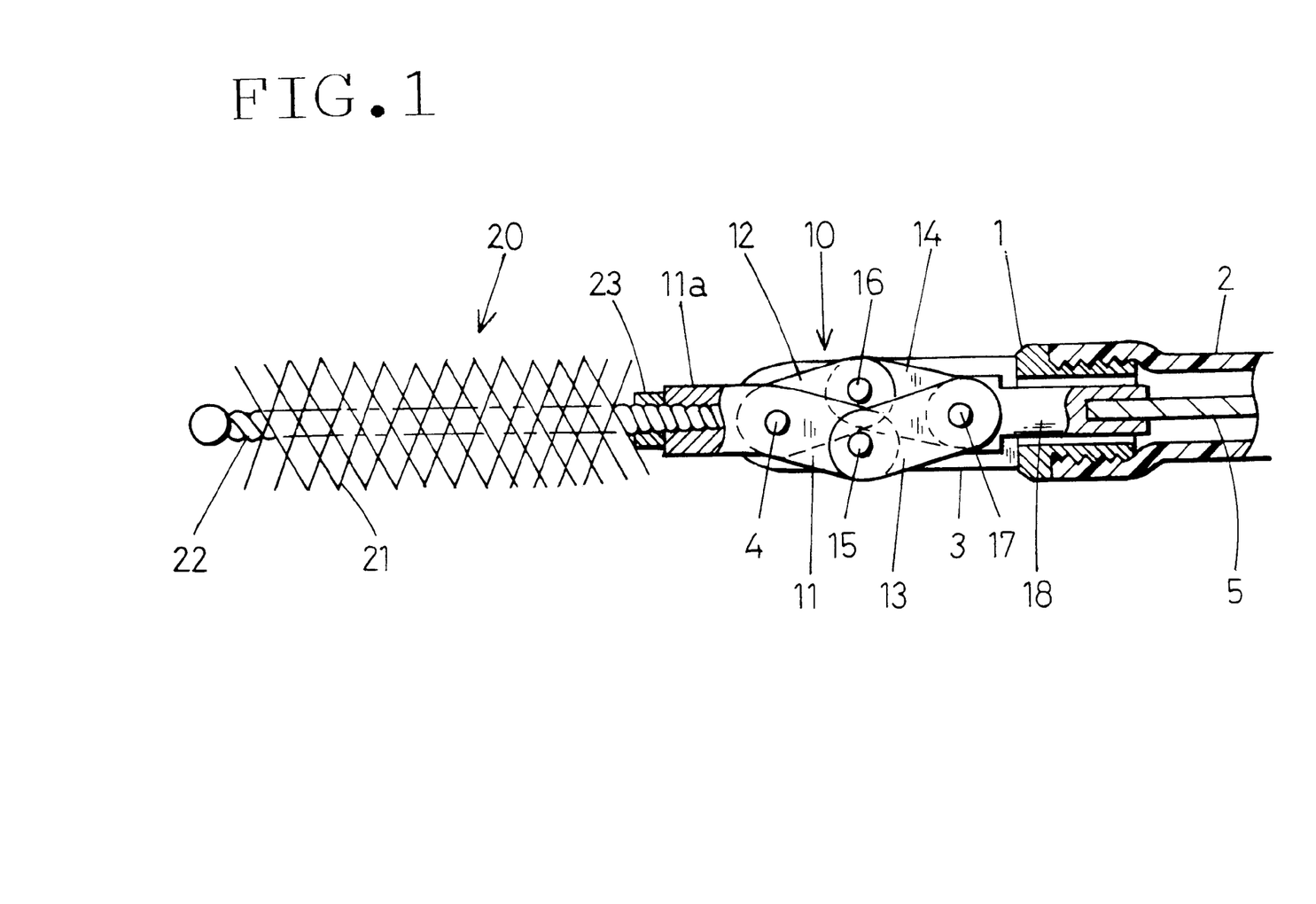
FIG. 1 is a sectional side view showing a distal end portion of a cytologic brush for an endoscope according to a first embodiment of the present invention.

FIG. 1 shows a distal end portion of a cytologic brush for an endoscope according to a first embodiment of the present invention. A flexible sheath 2 is removably inserted into an instrument-inserting channel of an endoscope (not shown). A metallic distal end block 1 is detachably connected to the distal end of the sheath 2 by thread engagement. The distal end block 1 has a large slit 3 cut from the forward end thereof.

The sheath 2 is formed from a tube of a synthetic resin material, for example, tetrafluoroethylene resin. However, the sheath 2 may be formed from a coil pipe that is formed by close-winding a thin metal wire with a uniform diameter.

A pivot shaft 4 is mounted on the distal end block 1 in such a way as to cross the distal end portion of the slit 3. A link mechanism 10 is placed in the slit 3. The link mechanism 10 is rotatably supported by the pivot shaft 4.

The link mechanism 10 has four link members 11, 12, 13 and 14 that are connected together so as to be rotatable relative to each other in the form of a pantograph. The first and second link members 11 and 12 are rotatably supported by the pivot shaft 4. The other connecting portions of the link mechanism 10 are rotatably connected by connecting shafts 15, 16 and 17.

A control wire 5 is axially movably inserted in the sheath 2. The control wire 5 is remote-controlled from an operating part (not shown) at the proximal end of the sheath 2. The distal end of the control wire 5 is firmly connected to a connecting rod 18. The forward end portion of the connecting rod 18 is rotatably connected to the connecting shaft 17, which connects the third and fourth link members 13 and 14 at the rear end of the link mechanism 10.

The first link member 11 of the link mechanism 10 is bent into an obtuse angle to extend forwardly at a portion thereof that is rotatably supported by the pivot shaft 4. A brush member 20 is connected to the forward end portion 11a of the first link member 11.

The brush member 20 is formed, for example, by twisting together two metal wires (brush shaft 22) with brush bristles 21 held therebetween. The brush bristles 21 project radially from the brush shaft 22.

The forward end portion 11a of the first link member 11 has a hole extending from the forward end thereof. The hole has an internal thread-shaped helical groove. The proximal end portion of the brush shaft 22 is screwed into the hole of the forward end portion 11a and thus detachably connected to the first link member 11. The brush shaft 22 has a stopper member 23 secured thereto in advance to limit the amount to which the brush shaft 22 is screwed into the hole of the forward end portion 11a.

In the cytologic brush for an endoscope according to this embodiment, when the link mechanism 10 is fully extended by pulling the control wire 5 to the full toward the proximal end of the sheath 2 as shown in FIG. 1, the brush shaft 22 faces forward in a straight-line form, lying on the prolongation of the axis of the distal end portion of the sheath 2. In this state, the cytologic brush is inserted into the instrument-inserting channel of an endoscope.

Figure 2:
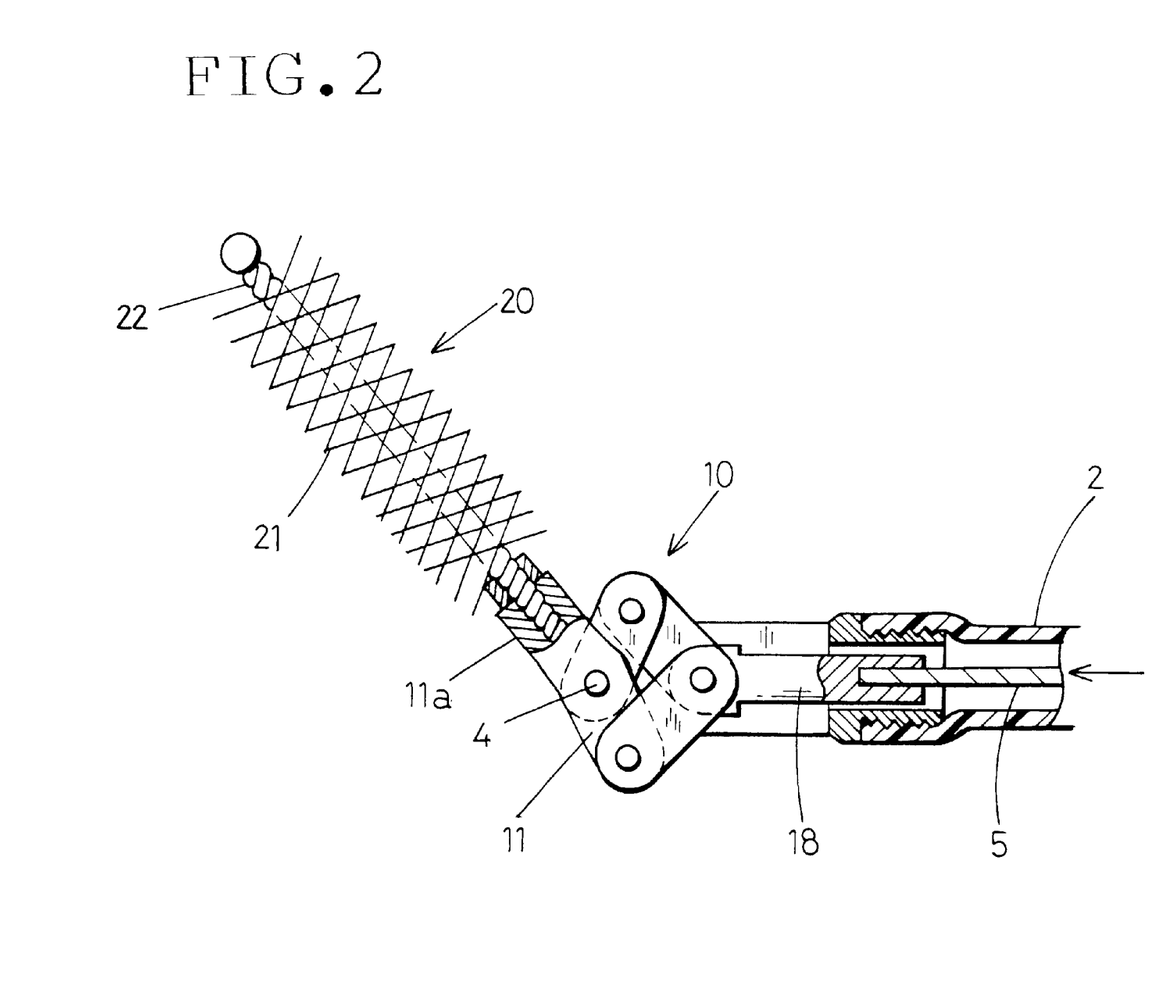
FIG. 2 is a sectional side view of the distal end portion of the cytologic brush according to the first embodiment of the present invention in a state where an operation of changing the direction of a brush member has been conducted.

When the control wire 5 is pushed toward the distal end of the sheath 2, as shown in FIG. 2, the link mechanism 10 is deformed in an axially collapsed shape. Accordingly, the brush shaft 22, which is connected to the forward end portion 11a of the first link member 11, swings around the pivot shaft 4. Consequently, the direction of the brush member 20 is changed.

In this way, the operation of changing the direction of the brush member 20 is performed through the link mechanism 10 by moving the control wire 5 back and forth. During this operation, no bending load is applied to the control wire 5. Therefore, even if the cytologic brush is used repeatedly, the control wire 5 does not develop an undesired bending habit, and the brush can maintain its intended performance.

Figure 3:
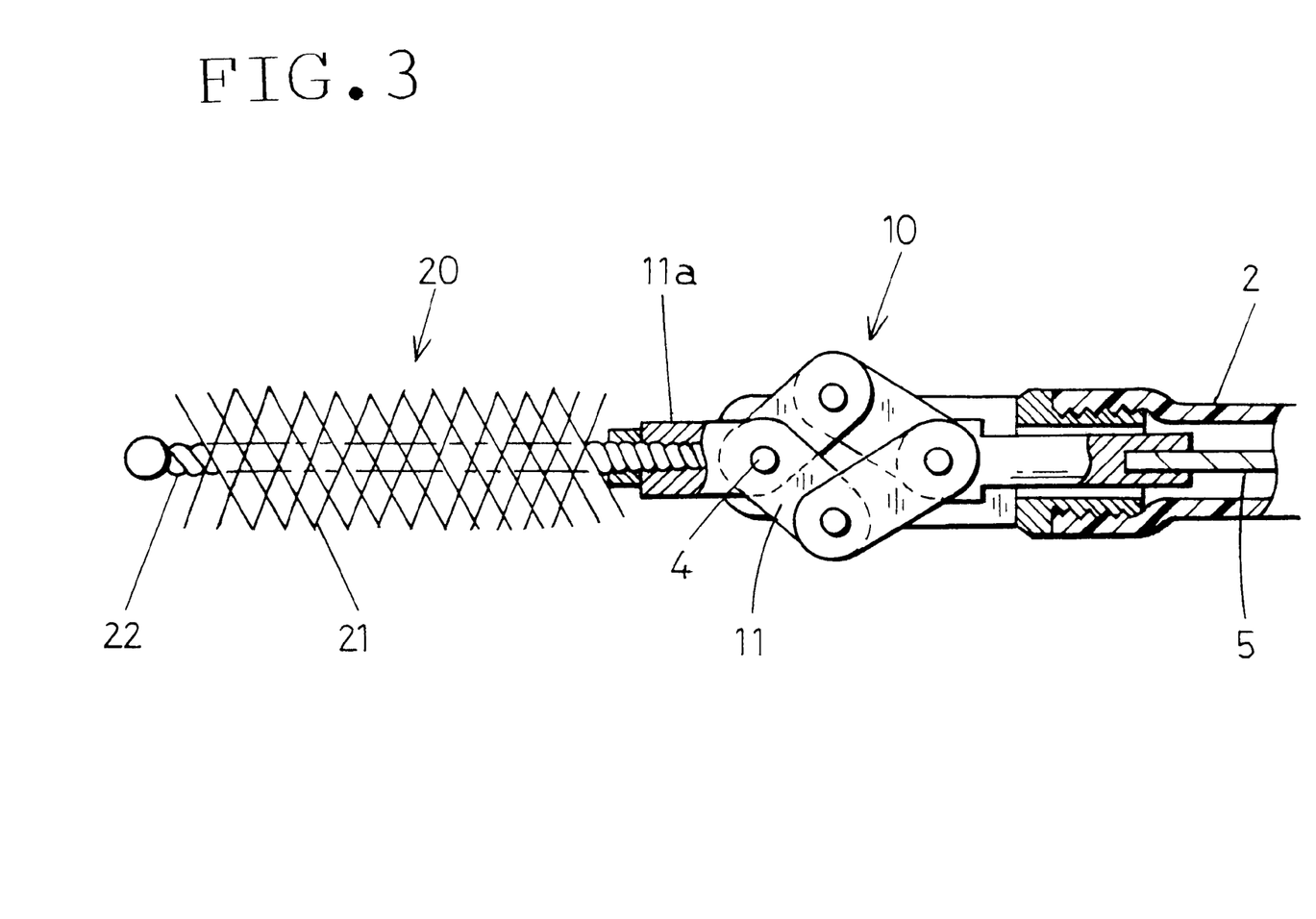
FIG. 3 is a sectional side view showing a distal end portion of a cytologic brush for an endoscope according to a second embodiment of the present invention.

FIG. 3 shows a distal end portion of a cytologic brush for an endoscope according to a second embodiment of the present invention. In this embodiment, when the control wire 5 is pushed slightly forward from the position where the control wire 5 is pulled to the full toward the proximal end of the sheath 2, the link mechanism 10 is slightly collapsed in the axial direction, and at this time, the brush shaft 22 faces forward in a straight-line form. Accordingly, the first link member 11 is bent into an obtuse angle smaller than in the first embodiment. The arrangement of the rest of the second embodiment is the same as in the first embodiment.

Figure 4:
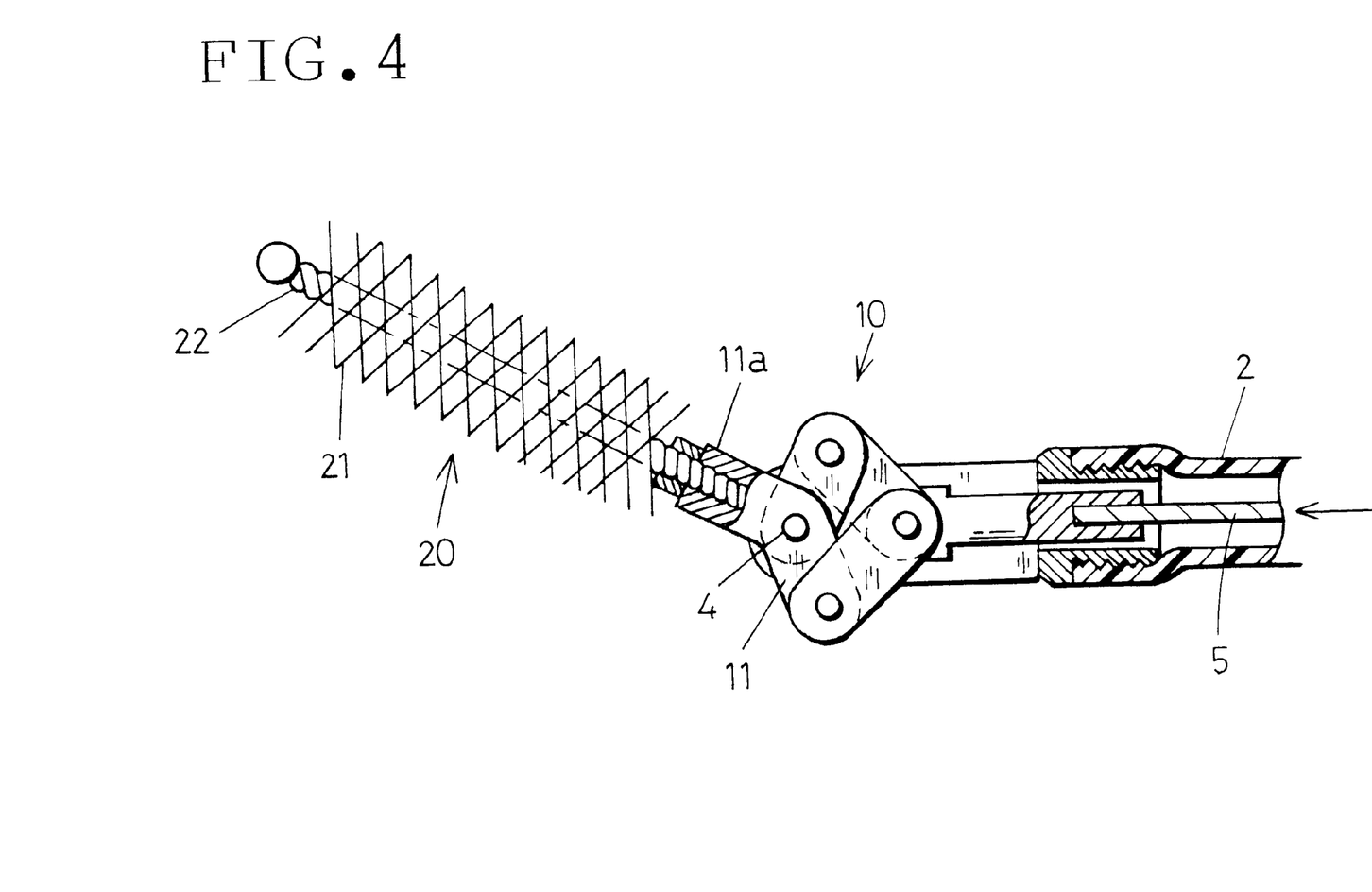
FIG. 4 is a sectional side view of the distal end portion of the cytologic brush according to the second embodiment of the present invention in a state where an operation of changing the direction of a brush member has been conducted.
Figure 5:
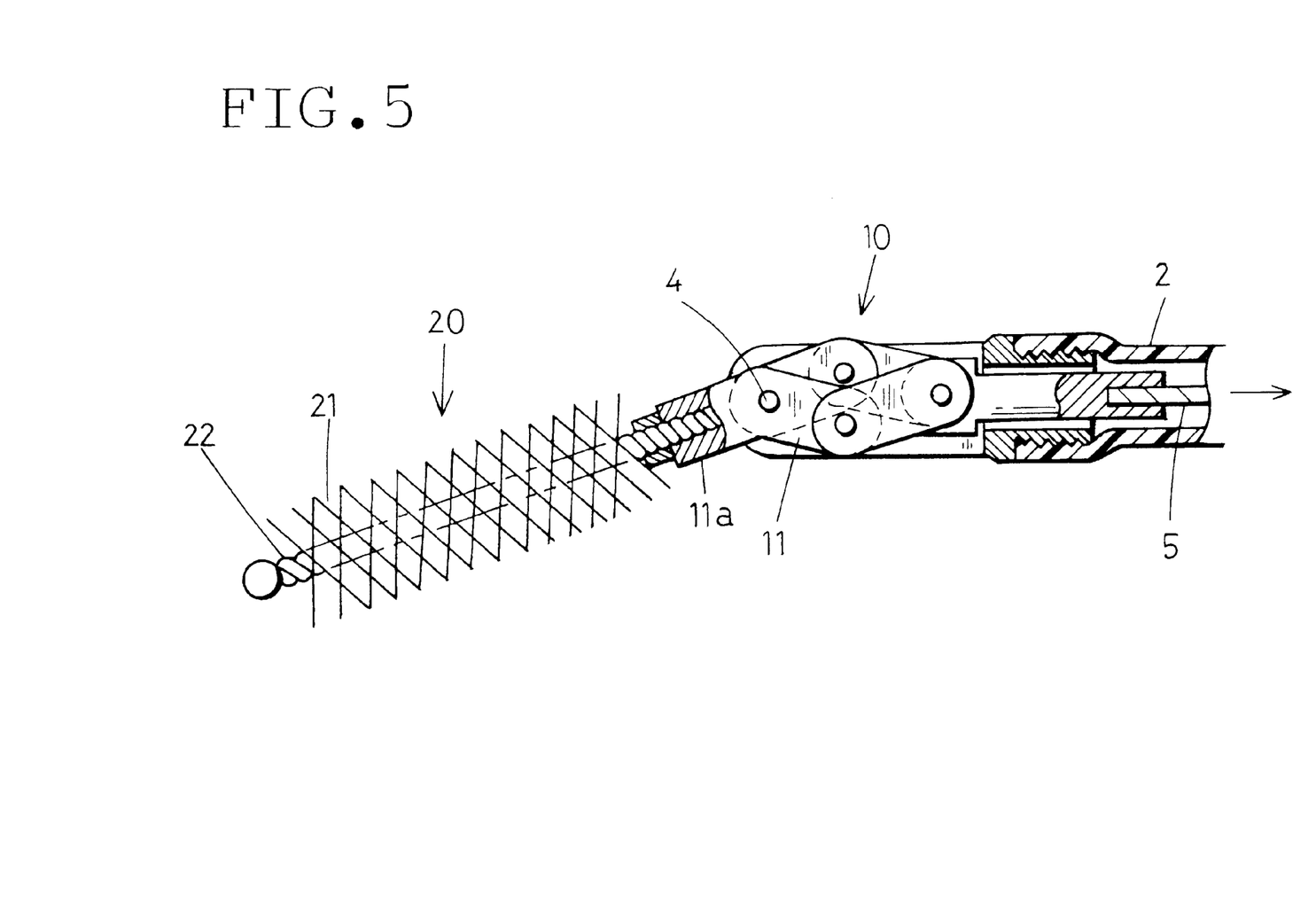
FIG. 5 is a sectional side view of the distal end portion of the cytologic brush according to the second embodiment of the present invention in a state where an operation of reorienting the brush member in the opposite direction has been conducted.

In the cytologic brush for an endoscope according to the second embodiment, arranged as stated above, when the control wire 5 is pushed from the proximal end of the sheath 2, as shown in FIG. 4, the brush shaft 22 rotates about the pivot shaft 4 in the same way as in the first embodiment. Consequently, the direction of the brush member 20 is changed. If the control wire 5 is pulled to the full toward the proximal end of the sheath 2, as shown in FIG. 5, the brush shaft 22 rotates as far as a position where the brush member 20 is reoriented in the opposite direction.

Thus, simply by moving a single control wire 5 back and forth in the axial direction, the brush shaft 22 is rotated about the pivot shaft 4, and thus the brush member 20 can be reoriented toward either of two sides of the prolongation of the axis of the distal end portion of the sheath 2.

Accordingly, in a trifurcated deep bronchial tube as shown in FIG. 8, the brush member 20 projecting from the distal end of the endoscope 50 can be readily inserted into any of the three tubes.

Figure 6:
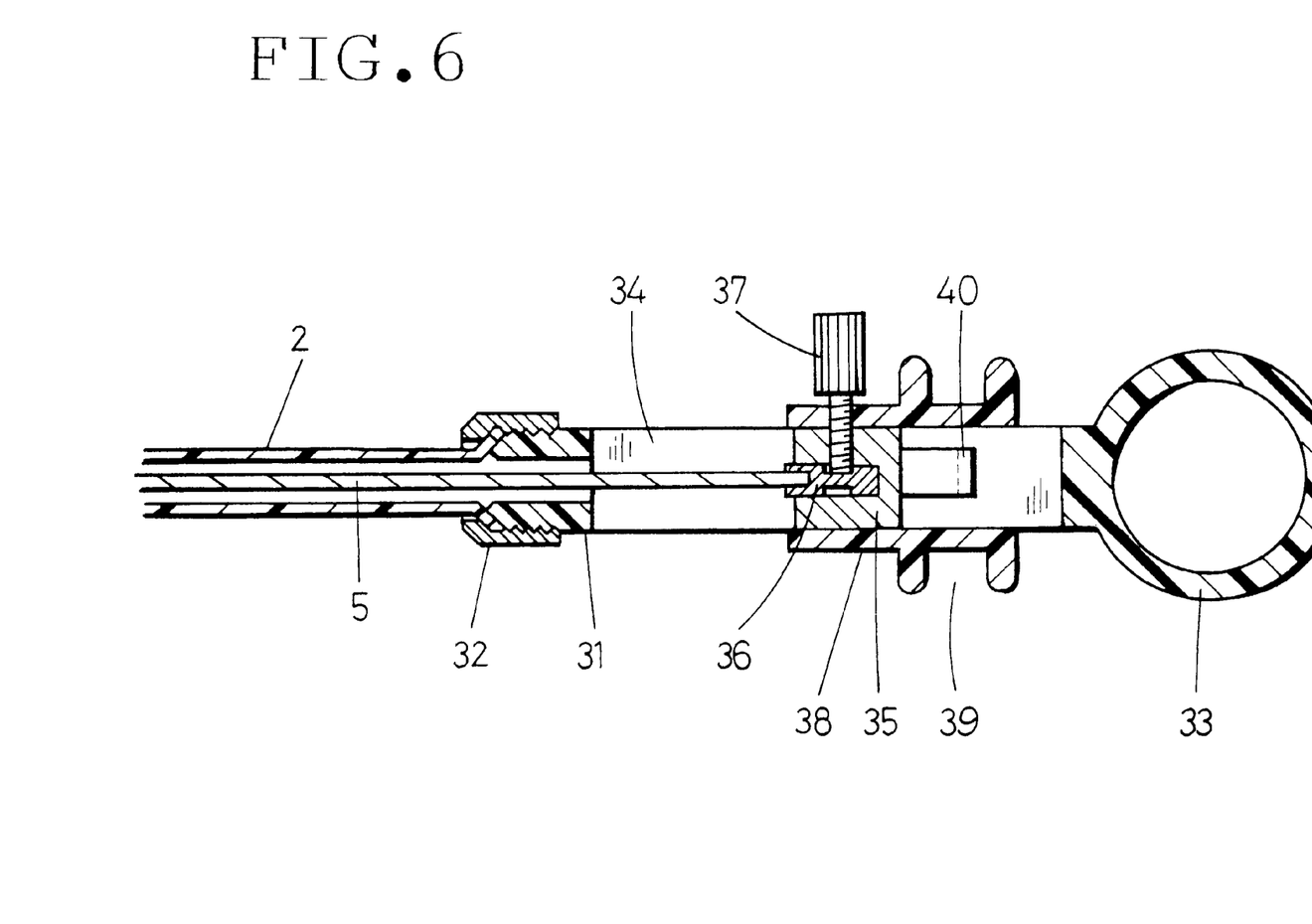
FIG. 6 is a sectional side view of an operating part of the cytologic brush according to the second embodiment of the present invention.
Figure 7:
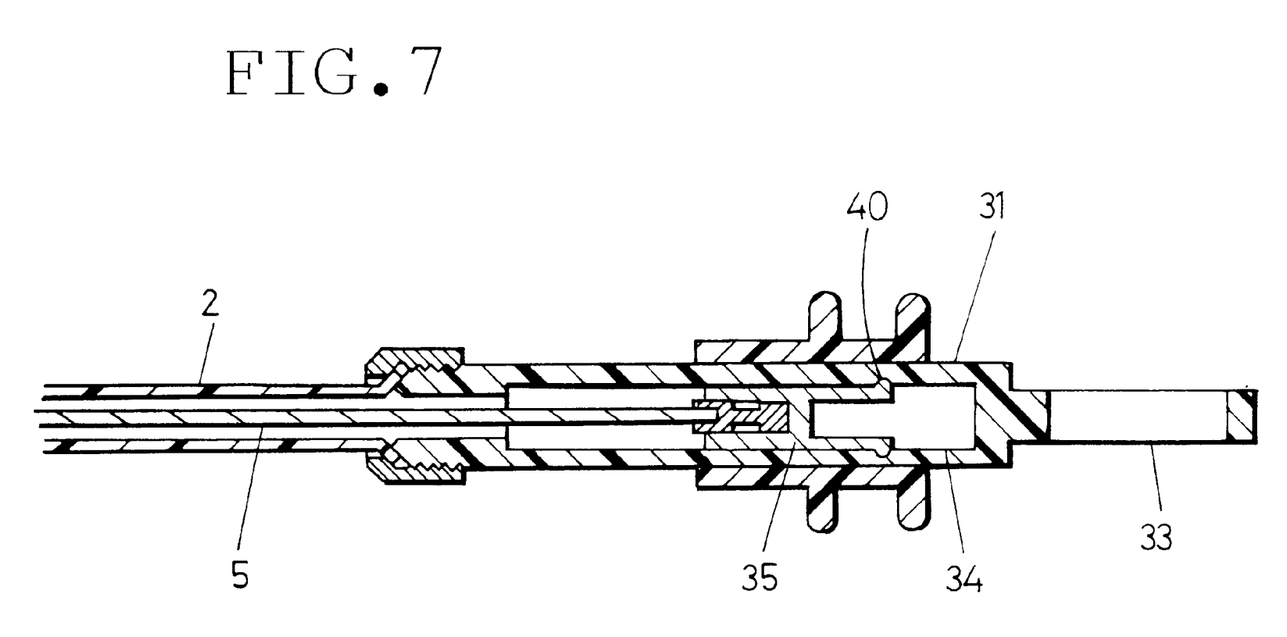
FIG. 7 is a sectional plan view of the operating part of the cytologic brush according to the second embodiment of the present invention.

FIG. 6 is a sectional side view showing an operating part of the cytologic brush for an endoscope according to the second embodiment of the present invention. FIG. 7 is a sectional plan view of the operating part.

The proximal end of the sheath 2 is expanded in a funnel shape. The proximal end of the sheath 2 is placed on a distal end portion of an operating part body 31 and secured thereto under pressure by a retaining nut 32 screwed onto the operating part body 31. Accordingly, the sheath 2 can be removed from the operating part body 31 by untightening the retaining nut 32 screwed to the operating part body 31.

A first finger engagement portion 33 is formed at the proximal end of the operating part body 31 to allow engagement with the operator's thumb. A longitudinally elongated slit 34 is formed in the operating part body 31. A wire-driving member 35 is fitted in the slit 34 so as to be slidable in the longitudinal direction of the slit 34. A wire end cap 36 is secured to the proximal end of the control wire 5. The wire end cap 36 is inserted into a hole provided in the center of the distal end of the wire-driving member 35. The wire end cap 36 is secured from a side thereof with a hand-operated screw 37.

Accordingly, if the hand-operated screw 37 is untightened, the control wire 5 can be separated from the wire-driving member 35. After use, the sheath 2 and the control wire 5 are separated from the operating part. At the distal end thereof also, the sheath 2 is separated from the distal end block 1. Consequently, the inside of the sheath 2, together with the control wire 5, can be thoroughly washed and disinfected.

A slider 38 is longitudinally slidably fitted on the outer surface of the operating part body 31. The slider 38 has a second finger engagement portion 39 for engagement with the operator's index and middle fingers. The slider 38 and the wire-driving member 35 are connected by the above-described hand-operated screw 37.

Accordingly, sliding the slider 38 in the longitudinal direction of the operating part body 31 causes the control wire 5 to move axially back and forth in the sheath 2. Consequently, the direction of the brush member 20 at the distal end of the sheath 2 changes.

A click 40 is provided to enable the brush member 20 to maintain the state of facing forward in a straight-line form.

The click 40 is formed from a projection formed at the distal end of a tongue extending rearward from the wire-driving member 35 in the slit 34 and a groove formed in the inner surface of the slit 34 so as to engage with the projection.

Consequently, when the brush member 20 extends straight ahead (i.e. when the brush shaft 22 lies on the prolongation of the axis of the distal end portion of the sheath 2), the sheath 2 and the control wire 5 are elastically locked relative to each other by the click 40. However, the arrangement may be such that the click 40 is engaged when the brush member 20 is in another position according to each particular purpose of use.

According to the present invention, the operation of changing the direction of the brush member is performed through the link mechanism by moving the control wire back and forth. No bending load is applied to the control wire to change the direction of the brush member. Therefore, even if the cytologic brush is used repeatedly, the control wire does not develop an undesired bending habit, and the brush exhibits excellent durability.

In addition, the brush member rotates about the pivot shaft of the link mechanism so that the direction of the brush member is changed to either of two sides of the prolongation of the axis of the distal end portion of the sheath. By virtue of this arrangement, the brush member can be inserted in a desired direction even in a narrow tubular cavity to collect a cytologic specimen by a simple mechanism using only one control wire.

While the invention has been described by reference to specific embodiments chosen for purposes of illustration, it should be apparent that numerous modifications could be made thereto by those skilled in the art without departing from the basic concept and scope of the invention.

What is claimed is:

1. A cytologic brush for an endoscope which has a flexible sheath removably inserted into an instrument-inserting channel of the endoscope, a single brush member provided at a distal end of said sheath, and a single control wire inserted in said sheath to change a direction of said single brush member from a proximal end of said sheath, said cytologic brush comprising:

a link mechanism provided at the distal end of said sheath, said single brush member being connected at a proximal end thereof to a forward link member of said link mechanism, said control wire being connected at a distal end thereof to a rear end of said link mechanism; and an operating part connected to the proximal end of said sheath to move said control wire back and forth at said operating part, said link mechanism is operated to move said single brush member to either of two sides of a prolongation of an axis of the distal end of said sheath by moving said single control wire back and forth in an axial direction.

2. A cytologic brush according to claim 1, wherein said brush member swings around a pivot shaft of said link mechanism.

3. A cytologic brush according to claim 1, wherein said single brush member is moved to one of said two sides of said prolongation of said axis of the distal end of said sheath by moving said single control wire in one of said back and forth directions and said single brush member is moved to the other of said two sides by moving said single control wire in the other of said back and forth directions.

4. A cytologic brush according to claim 3, wherein said operating part is provided with a click for elastically locking said brush member in a position where it lies on the prolongation of the axis of the distal end of said sheath.

5. A cytologic brush according to claim 2, wherein said link mechanism has four link members rotatably connected in a pantograph shape, said four link members including a link member that rotates about said pivot shaft, said link member being bent into an obtuse angle to extend forwardly at a portion thereof that is supported by said pivot shaft, the proximal end of said brush member being connected to said link member.

6. A cytologic brush according to claim 1, wherein said sheath is separable from said link mechanism.

7. A cytologic brush according to claim 1, wherein said sheath and said control wire are separable from said operating part.

* * * * *